United States Patent [19]
Jenkner et al.

[11] Patent Number: 6,020,448
[45] Date of Patent: Feb. 1, 2000

[54] N-[ω-(METHYL),ω-(SILYL)] ALKYL-N-ORGANOCARBOXAMIDES, OLIGOMERIC AND POLYCONDENSED SI-CONTAINING COMPOUNDS THEREOF, PROCESSES FOR THEIR PREPARATION, AND THEIR USE

[75] Inventors: Peter Jenkner; Albert Frings; Michael Horn; Jaroslaw Monkiewicz, all of Rheinfelden; Burkhard Standke, Loerrach, all of Germany

[73] Assignee: Huels Aktiengesellschaft, Marl, Germany

[21] Appl. No.: 09/098,530

[22] Filed: Jun. 17, 1998

[30] Foreign Application Priority Data

Jun. 17, 1997 [DE] Germany ............................ 197 25 516
Sep. 30, 1997 [DE] Germany ............................ 197 42 974

[51] Int. Cl.⁷ .................................................. C08G 77/04
[52] U.S. Cl. ................................ 528/26; 528/15; 528/12; 528/14; 427/387; 556/419; 556/436
[58] Field of Search .................................. 528/26, 15, 12, 528/14; 427/387; 556/419, 436

[56] References Cited

U.S. PATENT DOCUMENTS

| | | |
|---|---|---|
| 4,695,603 | 9/1987 | Inoue et al. . |
| 4,788,310 | 11/1988 | Stein et al. .............................. 556/419 |
| 5,373,079 | 12/1994 | Altes . |
| 5,508,360 | 4/1996 | Cifuentes et al. . |

FOREIGN PATENT DOCUMENTS

| | | |
|---|---|---|
| 0 392 509 | 10/1990 | European Pat. Off. . |
| 0 428 802 | 5/1991 | European Pat. Off. . |
| 0 450 900 | 10/1991 | European Pat. Off. . |
| 2 254 117 | 5/1974 | Germany . |

OTHER PUBLICATIONS

N. A. Anisimova, et al., Zh. Obshch. Khim, vol. 53, No. 5, pp. 1198–1199, 1983.
T. G. Shchekina, et al., Khim–Farm Zh., vol. 19, No. 2, pp. 165–167, 1985.
A. I. Albanov, et al., Zh. Obshch. Khim., vol. 52, No. 1, pp. 246–248, 1983.
Chemical Abstracts, vol. 103, (1985), 54137p.

*Primary Examiner*—Melvyn I. Marquis
*Attorney, Agent, or Firm*—Oblon, Spivak, McClelland, Maier & Neustadt, P.C.

[57] ABSTRACT

N-[ω-(methyl),ω-(silyl)]alkyl-N-organocarboxamides, oligomeric and polycondensed Si-containing compounds thereof, or mixtures of the corresponding monomeric, oligomeric and polycondensed Si-containing compounds. These materials are useful as, for example, adhesion promoters and for coating surfaces.

35 Claims, No Drawings

N-[ω-(METHYL),ω-(SILYL)] ALKYL-N-ORGANOCARBOXAMIDES, OLIGOMERIC AND POLYCONDENSED SI-CONTAINING COMPOUNDS THEREOF, PROCESSES FOR THEIR PREPARATION, AND THEIR USE

BACKGROUND OF THE INVENTION

1. Field of the Invention

The present invention relates to N-[ω-(methyl),ω-(silyl)] alkyl-N-organocarboxamides, to oligomeric or polycondensed Si-containing compounds thereof, or mixtures of the corresponding monomeric, oligomeric and polycondensed Si-containing compounds, and their use as adhesion promoters and for the coating of surfaces.

The invention also relates, firstly, to a process for preparing N-[ω(methyl),ω-(silyl)]alkyl-N-organocarboxamnides by a hydrosilylation reaction in the presence of a rhodium-containing catalyst, and, secondly, to a process for preparing oligomeric or polycondensed Si-containing compounds or mixtures thereof starting from N-[ω-(methyl),ω-(silyl)] alkyl-N-organocarboxarnides.

2. Description of the Background

Description of the use of monomeric and polycondensed N-(arkoxysilyl)organocarboxamides with alkylene, alkarylene, aralkylene, cycloalkylene or arylene groups inserted between the nitrogen of the carboxamide group and the silicon of the silyl group has to date been limited to just a few studies. In these studies, the hydrocarbon groups, with the exception of alkarylene and aralkylene groups, are predominantly in the form of ω,ω-substituted species.

Examples of known applications for such organosilylcarboxamides are their use as catalysts for preparing dialkyl carbonates from alkanols (EP 0 428 802 Al), their use as adhesion promoters or for the coating of surfaces (DE-C 22 54 117), or as additives in RTV silicone compositions (U.S. Pat. No. 4,695,603). In contrast, mono- and di-(N-methylacetamido)silanes substituted directly on the nitrogen of the acetamido group by silyl find application, for example, for the endgroup modification of hydroxyl-terminated polydimethylsiloxanes (U.S. Pat. No. 5,373,079) or are employed as free-radical hardeners in moisture-crosslinking, pressure-sensitive, silicone based adhesive systems (U.S. Pat. No. 5,508,360).

Cyclic N-ω-(alkoxysilyl)organocarboxamides with an unbranched alkyl group between the nitrogen and silicon have been obtained by hydrosilylation of cyclic ω-alkenylcarboxamides and hydridosilanes in the presence of a Pt catalyst, for example by hydrosilylating N-allyl-2-pyrrolidone with a hydridosilane of the type $HSiR'_n(OR)_{3-n}$ where R and R' are hydrocarbon groups and n is 1, 2 or 3 (EP 0 392 509 BI).

The hydrosilylation of cyclic ω-alkenylcarboxamides can also be carried out with SiH-functional polysiloxanes (EP 0 450 900 Al). Siloxanes modified in this way are used to treat glass fibers, as foam stabilizers, or are employed as additives for cosmetics.

A further synthesis route for the provision of cyclic silyl-substituted carboxamide is opened up by the amidoalkylation of N-(chloromethyl)amides with N-(trimethylsilyl)amines or -amides (N.A. Anisimova et al., Zh. Obshch. Khim. 53 (5) (1983), 1198–1199).

A cyclic N-1-(alkoxysilyl)organocarboxamide with a branched alkyl group between the nitrogen of the carboxamide and the silicon of the silyl group, N-1-(triethoxysilyl) ethyl-2-pyrrolidone, has been obtained by hydrosilylating N-vinyl-2-pyrrolidone with triethoxysilane in the presence of a rhodium complex catalyst in tetrahydrofuran, with a yield of 72.6%, and has been tested for its pharmacological properties (T.G. Shchekina et al., Khim.-Farm Zh., 19 (2) (1985), 165–167; CA Vol. 103 (1985), 54137 p).

In addition, syntheses of monomeric and oligomeric methylsilyl-lactam structures starting from [chloro(methyl)] methyl/chlorosilanes (A. I. Albanov et al., Zh. Obshch. Khim. 52 (1) (1983), 246–248) or [chloro(methyl)]methyl/ methoxysilanes (L. M. Khananashvili et al., Zh. Obshch. Khim. 52 (9) (1982), 2095–2097) are known. In general, the demand nowadays is for synthesis routes with a very low proportion of chlorine-containing starting materials.

In many products an extremely low chloride content is desired. Higher chloride contents may adversely affect the hydrolysis characteristics and the storage stability of organosilanes and organosiloxanes. Furthermore, in many possible fields of application, for example supports or components for electronic circuits, even small amounts of chloride are undesirable, so that, for example, products obtainable in accordance with DE-C 22 54 117 are nowadays of only limited commercial interest for such applications.

DE-C 22 54 117 discloses the hydrolysis of β-chloroethylalkoxysilanes and the reaction of the resulting siloxane with an alkylamine or with other substitution products of ammonia.

Another disadvantage of many organopolysiloxanes is their relatively poor solubility, especially in water.

SUMMARY OF THE INVENTION

It is an object of the present invention to provide simple and economical access to N-[ω-(methyl), ω-(silyl)]alkyl-N-organocarboxamides and to optionally polycondensed Si-containing compounds thereof. A particular concern in this context was to keep the proportion of chlorine-containing starting materials as low as possible.

It has now surprisingly been found that N-[ω-(methyl), ω-(silyl)]alkyl-N-organocarboxamides of the general formula I:

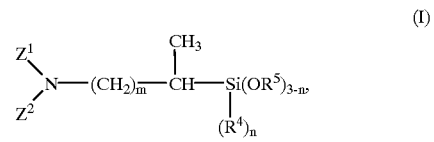

in which

Z¹ is

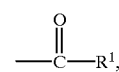

Z² is defined like R², or

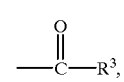

or

Z¹ and Z² are bridged to give a ring of the following formula, i.e., Z¹ and Z², together with the nitrogen atom to which they are bonded, form one of the groups shown below:

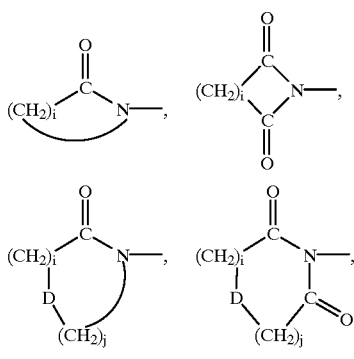

where D is a HN, O, S, SO or $SO_2$ group and i and j are identical or different and are an integer from 0 to 7, and the size of the ring is $\leq 9$ members, $R^1$, $R^2$, $R^3$, $R^4$ and $R^5$ are identical or different, and are each a hydrogen atom or a linear, branched or cyclic alkyl group having 1 to 8 C. atoms or an aryl group having 6 to 10 C. atoms, and $R^5$ can be either a hydrogen atom or a linear, branched or cyclic alkyl group having 1 to 8 C atoms or an aryl group having 6 to 10 C atoms, and m is an integer from 0 to 16, and n is an integer from 0 to 3.

These compounds are obtainable in a simple and economical manner by reacting an ω-alkylenecarboxamide of the general formula IV:

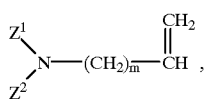
(IV)

in which $Z^1$, $Z^2$, $R^1$, $R^2$, $R^3$ and m are as defined above for formula I, with a hydridosilane of the general formula V:

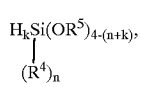
(V)

in which $R^4$ and $R^5$ are as defined above for formula I and n is an integer 0, 1, 2 or 3, k is an integer 1, 2, 3 or 4 and (n+k) is $\leq 4$, in the presence of metallic rhodium on an active carbon support, $(Ph_3P)_3Rh(CO)H$, $(Ph_3P)_3RhCl$ or $[Rh(1,5\text{-}cyclooctadiene)Cl]_2$ or of a mixture which comprises at least one of the above-mentioned Rh complex compounds and at least one Pt complex compound as catalyst, and working up the resulting product mixture with yields of up to, for example, 87%.

A more complete appreciation of the invention and many of the attendant advantages thereof will be readily obtained as the same becomes better understood by reference to the following detailed description.

DETAILED DESCRIPTION OF THE INVENTION

It can be advantageous if at least one of the above-mentioned rhodium complex compounds is employed in a mixture with at least one platinum complex compound, such as $(Ph_3P)_3PtCl_2$ or $(Ph_3P)_4Pt$ or those based on hexachloroplatinic acid, especially as acetone, cyclohexanone or isopropanol complexes. Pt complex compounds and Rh complex compounds are preferably employed in a proportion by mass to one another of from 1:10 to 5:1.

Further advantages of the novel synthesis route for preparing N-[ω(methyl),ω-(silyl)]alkyl-N-organocarboxamides are short reaction times, the possibility of a low-cost "one-pot" process, and the avoidance of fairly large amounts of inorganic salts, especially chloride-containing salts, as by-products.

Hydrosilylation reactions lead in general predominantly to α-adducts, is although β-adducts may also be formed as by-products, for example:

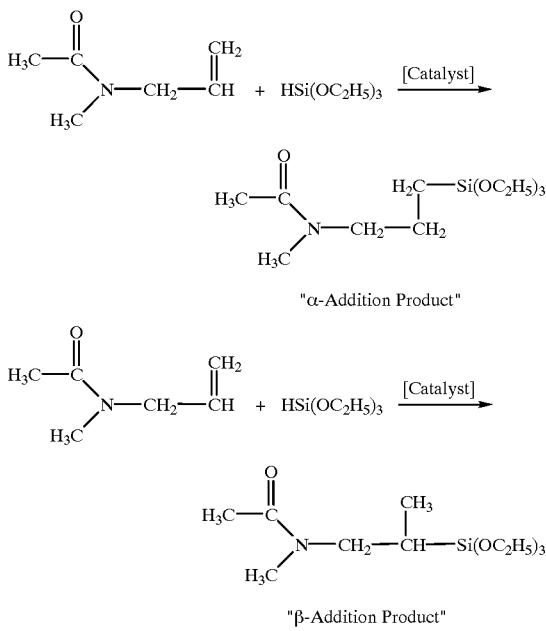

In the novel preparation it has surprisingly been found that during the reaction of ω-alkenyl-N-organocarboxamides with alkoxysilanes using said Rh catalysts or mixtures of Rh and Pt complex compounds the hydrosilylation takes place with high selectivity at the ω position. With the novel use of these catalysts, this selectivity is usually >80 GC-WLD for β adduct relative to the isomeric a product, further isomers generally occurring only in an order of magnitude of less than 3 GC-WLD area %. In addition, the α/β isomers can be resolved in the course of working up the product mixture which is obtained in the reaction, so that in this way the pure N-[ω-(methyl),ω-(silyl)]alkyl-N-organocarboxamides can be obtained in a simple and economical manner.

$(Ph_3P)_3Rh(CO)H$ has been found to be a particularly suitable catalyst system. The product mixture obtained in the present process is worked up suitably by distillation under atmospheric or reduced pressure.

Accordingly, given the use of essentially chlorine-free precursors in the present process, it is also possible advantageously to prevent the production of chlorine-containing residues when working up the product.

The present invention therefore provides N-[ω (methyl),ω (silyi)]alkyl-organocarboxamides of the general formula I:

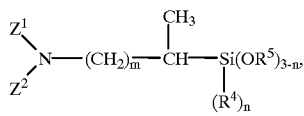

(I)

in which $Z^1$, $Z^2$, $R^1$, $R^2$, $R^3$, $R^4$, $R^5$, m and n are as defined above for formula I, with the exception of noncyclic compounds of formula I where m is 1 and N-1-(triethoxysilyl) ethyl- 2-pyrrolidone.

The invention therefore also provides a process for preparing N-[ω(methyl),ω-(silyl)]alkyl-N-organocarboxamides of the general formula I by a hydrosilylation reaction in the presence of a rhodium-containing catalyst, which comprises reacting an ω-alkylenecarboxamide of the general formula IV:

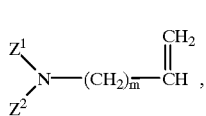

(IV)

in which $Z^1$, $Z^2$, $R^1$, $R^2$, $R^3$ and m are as defined above for formula I, with a hydridosilane of the general formula V:

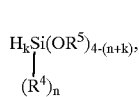

(V)

in which $R^4$, $R^5$, n, k and (n+k) are as defined above for formula V, in the presence of metallic rhodium on an active carbon support, $(Ph_3P)_3Rh(CO)H$, $(Ph_3P)_3RhCl$ or $[Rh(1, 5\text{-cyclooctadiene})Cl]_2$ or of a mixture comprising at least one of the abovementioned Rh complex compounds and at least one Pt complex compound, as catalyst, and working up the resulting product mixture.

The following may be mentioned as examples of preferred precursors in the novel process-preferred ω-alkylenecarboxamides of general formula IV are: N-vinylacetamide, N-methyl-N-vinylacetarnide, N-methyl-N-vinylformamide, N-vinylformamide, N-allyl-2-(dimethylamino)acetarnide, N-vinylphthalimide, N-vinyl-2-pyrrolidone, N-vinyl-2-piperidinone, N-vinyl-2-azocinone and N-vinyl-2-azepinone and also N-vinyl-2-azoninone.

The following are preferred hydridosilanes of general formula V: trimethoxysilane, triethoxysilane, tri-i-propoxysilane, tri-n-propoxysilane, tri-sec-butoxysilane, tri-i-butoxysilane, tri-t-butoxysilane, tri-n-butoxysilane, tris(2-ethylbutoxy)silane, tris(2-ethylhexoxy)silane, tris(2-methoxyethoxy)silane, methyidimethoxysilane, methyldiethoxysilane, phenyldimethoxysilane, phenyldiethoxysilane, methylphenylmethoxysilane, methylphenylethoxysilane, dimethylmethoxysilane, dimethylethoxysilane, methyldi-n-propoxysilane, methyldi-n-propoxysilane, methyldi-sec-butoxysilane, methyldi-n-butoxysilane, methyldi-i-butoxysilane, methyldi-t-butoxysilane, methylbis(2-methoxyethoxy)silane, dimethyl-n-propoxysilane and dimethyl-i-propoxysilane.

The novel process is generally carried out as follows. In general, the catalyst system is added to the precursor of formula IV and the mixture is stirred; this is judiciously carried out already under inert gas, preferably $N_2$. The initial charge can then be heated. and the precursor of formula V added dropwise. Alternatively, the precursor of formula V including the catalyst can be introduced as the initial charge and, judiciously after heating, the precursor of formula IV can be added dropwise.

In the novel process the rhodium-containing catalyst is added to the ω-alkylenecarboxamide of formula IV in a proportion by mass of preferably from 1:1000 to 1:100,000, with particular preference in a proportion by mass of from 1:3000 to 1:50,000, and with very particular preference in a proportion by mass of from 1:5000 to 1:30,000.

In the novel process the reaction can be carried out in the presence of an inert hydrocarbon or hydrocarbon mixture. The novel reaction is preferably carried out in toluene or xylene or n-decane.

The reaction is usually carried out with thorough mixing at a temperature in the range between room temperature and 200° C., preferably between 80 and 200° C., and over a period of from 0.25 to 24 hours, preferably over a period of from 0. 5 to 10 hours. The crude product obtained is subsequently worked up, work-up in the novel process preferably taking place by distillation.

The following are examples of preferred products of general formula I of the novel process: N-1-(trimethoxysilyl)ethylacetamide, N-1-(triethoxysilyl) ethylacetamide, N-1-(trimethoxysilyl)ethyl-N-methylacetamide, N-1(triethoxysilyl)ethy-N-methyl-acetamide, N-1-(trimethoxysilyl)ethyl-N-methylformamide, N-1-(triethoxysilyl)ethylformamide, N-1-(triethoxysilyl) ethyl-N-methylformamide, N-1-(trimethoxysilyl) ethylformamide, N-1-(trimethoxysilyl)ethyl-2-pyrrolidone, N-1-(triethoxysilyl)ethyl-2-pyrrolidone, N-1-(methyldimethoxysilyl)ethyl, N-methylacetamide, N-1-(dimethylmethoxysilyl)ethyl-N-methylacetamide, N-1-(tri-i-propoxysilyl)ethylacetamide, N-1-(tri-i-propoxysilyl) ethyl-N-methylacetamide, N-1-(tri-i-propoxysilyl)ethyl-2-pyrrolidone, N-1-(methyldimethoxysilyl)ethyl-2-piperidinone, N-1-(triethoxysilyl)ethyl-2-azepinone, N-1-(tris(2-methoxyethoxy)silyl)ethyl-N-methylacetamide, N-1-methyldiethoxysilyl)ethyl-N-methylacetamide, N-1-(methyldiethoxysilyl)ethyl-2-pyrrolidone, N-1-(methyldiethoxysilyl)ethyl-2-pyrrolidone.

In general, the novel compounds of formula I are readily soluble in inert organic solvents, such as cyclohexane, heptane or toluene, and can be applied to substrates from such solutions by, for example, dipping, brushing or spraying onto various substrate surfaces. With particular advantage, N-[ω(methyl),ω-(silyl)]alkyl-N-organocarboxamides of the general formula I can be employed as adhesion promoters in the coating of inorganic substrates, preferably metals, such as copper, iron or silver, or glass, with respect to polyamides, polyimides, epoxy resins or polyurethanes.

In particular, the novel compounds of formula I are also readily soluble in water, preferably with catalysis by acid or base and with simultaneous hydrolysis to the corresponding silanols and, in parallel therewith, oligomerization. In this context the degree of oligomerization is suitably below 50, preferably from 2 to 20. Hence the aqueous solutions of active substance, which are suitably employed in a concentration range from 0.01 to 50% by weight, preferably from 0.05 to 15% by weight and, with particular preference, from 0.1 to 5% by weight, can be prepared rapidly and simply and can likewise be applied by, for example, dipping, brushing or spraying to the desired substrate surface. Using these active substances it is possible to enhance the surface coverage of a wide variety of substrates. The partial replacement of the water by an alcohol, such as methanol, ethanol or isopropanol, depending on the surface energy of the substrate to be treated, also makes it possible to adapt the wettability. By the application, optionally by means of doctor knives, of aqueous solutions, preferably having active substance concentrations of from 0.05 to 15% by weight, to glass or metals it is possible to produce clear, elastic, moisture-resistant, ceramic films which in addition possess high scratch resistance, for protecting and for modifying the optical properties of the respective substrates.

Preferred compounds of the general formula I, as may be present in particular in hydrolysates and in aqueous or solvent-containing mixtures thereof, are also, however, the following Si-containing compounds: N-1-(trimethoxysilyl) ethyl-N-methylformamide, N-1-(triethoxysilyl) ethylformamide, N-1-(triethoxysilyl)ethyl-N-methylformamide, N-1-(trimethoxysilyl)ethylformamide, N-1-(trimethoxysilyl)ethylacetamide, N-1-(triethoxysilyl) ethylacetamide, N-1-(trimethoxysilyl)ethyl-N-methylacetamide, N-1-(triethoxysilyl)ethyl-N-methylacetamide, N-1-(trimethoxysilyl)ethyl-2-pyrrolidone, N-1-(triethoxysilyl)ethyl- 2-pyrrolidone, N-1-(methyldimethoxysily 1)ethyl-N-methylacetamide, N-1-(dimethylmethoxysilyl)ethyl-N-methyl acetamide, N-1-(tri-i-propoxysilyl)ethylacetamide, N-1-(tri-i-propoxysilyl) ethyl-N-methylacetamide, N-1-(tri-i-propoxysilyl)ethyl-2-pyrrolidone, N-1-(methyldimethoxysilyl)ethyl-2-piperidinone, N-1-(triethoxysilyl)ethyl-2-azepinone, N-1-(tris(2-methoxyethoxy)silyl)ethyl-N-methylacetamide, N-1-(methyldiethoxysily 1)ethyl-N-methylacetamide, N-1-(methyldimethoxysilyl)ethyl-2-pyrrolidone, N-1-(methyldiethoxysilyl)ethyl-2-pyrrolidone, N-1-(trihydroxysilyl)ethyl-N-methylformamide, N-1-(dihydroxymethoxysilyl)ethyl-N-methylformamnide, N-1-(hydroxydimethoxysilylethyl-N-methylformamide, (diethoxyhydroxysilyl)ethyl-N-methylformrnamide, N-1-(ethoxydihydroxysilyl)ethyl-N-methylformamide, N-1-(trihydroxysilyl)ethyl-N-methylacetamide, N-1-(dihvdroxymethoxysilyl)ethyl-N-methylacetamide, N-1-(hydroxydimethoxysilyl)ethyl-N-methylacetamide, N-1-(diethoxyhydroxysilyl)ethyl-N-methylacetamide, (ethoxydihydroxysilyl)ethyl-N-methylacetamide, N-1-(trihydroxysiiyl)ethyl-2-pyrrolidone, N-1-(dihydroxymethoxysilyl)ethyl-2-pyrrolidone, N-1-(dihydroxyethoxysilyl)ethyl-2-pyrrolidone, N-1-(hydroxydiethoxysilyl)ethyl-2-pyrrolidone, N-1-(hydroxydimethoxysily 1 )ethyl-2-pyrrolidone, N-1-(dihydroxy-i-propoxysilyl)ethyl-2-pyrrolidone, N-1-(hydroxydi-i-propoxysilyl)ethyl-2-pyrrolidone, N-1-(methyldihydroxysilyl)ethyl-N-methylacetamide, N-1-(methylhydroxymethoxysilyl)ethyl-N-methylacetamide, N-1-(methylhydroxyethoxysilyl)ethyl-N-methylacetamide, N-1-(dimethylhydroxysilyl)ethyl-N-methylacetamide, N-1-(methyldihydroxysilyl)ethy 1-2-piperidinone, N-1-(methyletboxyhydroxysilyl)ethyl-2-piperidinone, N-1-(trihydroxysilyl)ethyl-2-azepinone, N-1-(dihydroxyethoxysilyl)ethyl-2-azepinone, N-1-(hydroxydiethoxysilyl)ethyl-2-azepinone, N-1-(methyidihydroxysilyl)ethyl2-pyrrolidone, N-1-(methylhydroxymethoxysilyl)ethyl-2-pyrrolidone, N-1-(methy[hydroxyethoxysilyl)ethyl-2-pyrrolidone.

It has also been found that oligomeric Si-containing compounds of the general formula II:

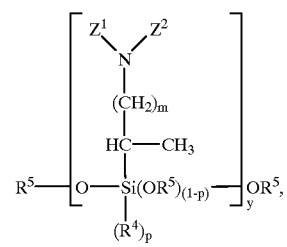

(II)

in which $Z^1$ is

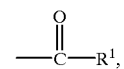

$Z^2$ is defined like $R^2$, or

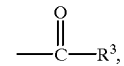

or $Z^1$ and $Z^2$ are bridged to give a ring of the following formula, i.e., $Z^1$ and $Z^2$, together with the nitrogen atom to which they are bonded, form one of the groups shown below:

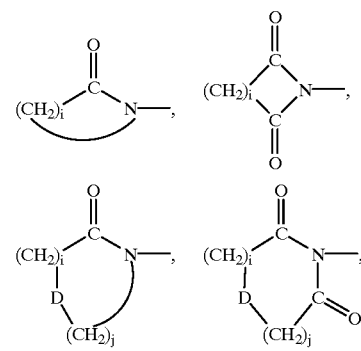

where D is a HN, O, S, SO or $SO_2$ group, and i and j are identical or different and are an integer from 0 to 7, and the size of the ring is $\leq 9$ members, $R^1$, $R^2$, $R^3$, $R^4$ and $R^5$ are identical or different and are each a hydrogen atom or a linear, branched or cyclic alkyl group having 1 to 8 C atoms or an aryl group having 6 to 10 C atoms, and $R^5$ can be either a hydrogen atom or a linear, branched or cyclic alkyl group having 1 to 8 C atoms, or an aryl group having 6 to 10 C atoms, m is an integer from 0 to 16, p is an integer 0 or 1, and y is an integer from 2 to 50, preferably from 2 to 20, or polycondensed Si-containing compounds of the general formula III:

(III)

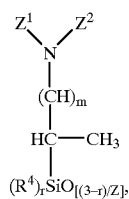

in which $Z^1$ is

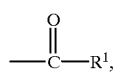

$Z^2$ is defined like $R^2$, or

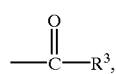

or $Z^1$ and $Z^2$ are bridged to give a ring of the following formula, i.e., $Z^1$ and $Z^2$, together with the nitrogen atom to which they are bonded, form one of the groups shown below:

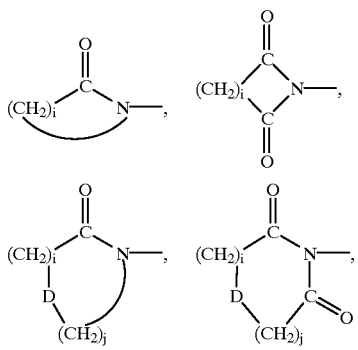

where D is a HN, O, SO or $SO_2$ group, and i and j are identical or different and are an integer from 0 to 7, and the size of the ring is $\leq 9$ members, $R^1$, $R^2$, $R^3$ and $R^4$ are identical or different and are each a hydrogen atom or a linear, branched or cyclic alkyl group having 1 to 8 C atoms or an aryl group having 6 to 10 C atoms, m is an integer from 0 to 16, and r is an integer 0 or 1, or mixtures which comprise Si-containing compounds of the general formulae I, II and/or III, are likewise obtainable in a simple and economical manner by controlled hydrolysis of at least one N-[ω-(methyl), ω-silyl)]alkyl-N-organocarboxamide of the general formula I:

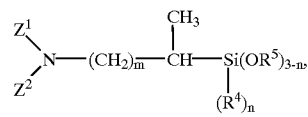

in which $Z^1$, $Z^2$, $R^1$, $R^2$, $R^3$, $R^4$, $R^5$, m and n are as defined above for formula I, in water or in an alcohol/water rixture in which alcohol and water are present in a proportion by mass to one another of from 1:100 to 100:1, preferably from 70:30 to 90:10, and the water or the alcohol/water mixture is adjusted to a pH <7 by addition of an inorganic or organic acid or of an acidic salt or to a pH >7 by addition of a base or of a basic salt, the compound(s) of formula I and water being employed in a proportion by mass to one another of from 0.1:99.9 to 99.99:0.01, preferably from 2:98 to 90:10.

A particular advantage of the novel Si-containing compounds of the formula II or III, or mixtures and formulations thereof, which may also comprise monomers of formula I and/or corresponding silanols, is, furthermore, their outstanding storage stability, especially that of those formulations based on water and/or alcohol.

The present invention therefore also provides oligomeric Si-containing compounds of the general formula II:

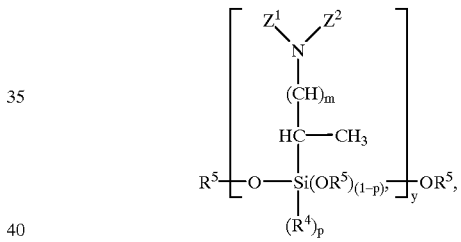

in which $Z^1$, $Z^2$, $R^1$, $R^2$, $R^3$ $R^4$, $R^5$, m, p and y are as defined above for formula II, and also polycondensed Si-containing compounds of the general formula III

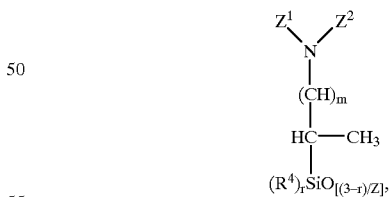

in which $Z^1$, $Z^2$, $R^1$, $R^2$, $R^3$, $R^4$, m and r are as defined above for formula III, with the exception of compounds of formula III where m is 1 which are noncyclic in terms of $Z^1$ and $Z^2$.

The present invention relates, furthermore, to a process for preparing Si-containing compounds of the general formulae II or III or a mixture comprising Si-containing compounds of the general formulae I, II and/or III, which comprises subjecting at least one N-[ω-(methyl),(ω-(silyl)] alkyl-N-organocarboxamide of the general formula I:

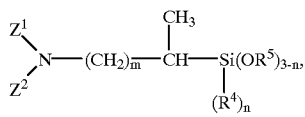

in which $Z^1, Z^2, R^1, R^2, R^3, R^4, R^5$, m and n are as defined above for formula I, to controlled hydrolysis in water or an alcohol/water mixture in which alcohol and water are present in a proportion by mass to one another of from 1:100 to 100:1, preferably from 70:30 to 90:10, and the water or the alcohol/water mixture is adjusted to a pH <7 by addition of an inorganic or organic acid or of an acidic salt or to a pH >7 by addition of a base or of a basic salt, and the compound(s) of formula I and water are employed in a proportion by mass to one another of from 0.1:99.9 to 99.99:0.01, preferably from 2:98 to 90:10.

In the novel hydrolysis process the general procedure is to introduce water or an alcohol/water mixture as the initial charge and to adjust the pH to a value $\geq 1$ and <7 or >7 and <12 by adding an acid or base.

In the novel hydrolysis process use is suitably made of formic, acetic or citric acid or sodium acetate or sodium formate to establish the pH; this can also be done, however, using aqueous solutions of hydrogen chloride or sodium hydroxide.

In the novel hydrolysis process it is preferred to use an alcohol or an alcohol mixture where at least one of the alcohols corresponds to at least one alkoxy group of the compound of formula I employed; particular preference is given to the use of methanol, ethanol, n-propanol, isopropanol, n-butanol, isobutanol, sec-butanol, t-butanol, 2-methoxyethanol or 2-ethylhexanol.

In the novel hydrolysis process the pH of the water or of the alcohol/water mixture is adjusted in particular to a value of $\geq 2$ and $\leq 6$ and the hydrolysis is conducted in the pH range of $\geq 2$ and $\leq 6$. In accordance with the invention it is preferred to employ the compound(s) of formula I and water in a proportion by mass to one another of from 2:98 to 90:10. Preferred examples of compounds of the general formula I have already been indicated above.

The compounds of formula I, preferably in small portions, are generally added with stirring to the solution prepared beforehand. Alternatively, the N-[ω-(methyl),ω-(silyi)]alkyl-N-organocarboxamide of the formula I can be introduced as the initial charge and water or an alcohol/water mixture added, in which case thorough mixing is suitably ensured.

The hydrolysis can be conducted at a temperature from 0 to 100° C., preferably from 25 to 80° C. Active substance solutions obtained in this way may, furthermore, be adjusted by distillative procedures to alcohol contents of 0.01 to 90% by weight, preferably from 0.5 to 50% by weight. Alcohols particularly suitable for this purpose are methanol, ethanol and isopropanol.

Examples of preferred compounds of the general formulae II and III can be designated in general as set out below. Preferred compounds of general formula II are: n-{α,ω,-diethoxyoligo [(1-(2-pyrrolidonyl)ethylethoxy)siloxane]) }cyclo-{{αω,-diethoxyoligo[(1-(2-pyrrolidonyl) ethylethoxy)siloxane]}, n-{α, ω-diethoxyoligo[(1-(N-methylacetarnido)ethylethoxy)siloxane]),cyclo-{α,ω-diethoxyoligo[(1-(N-methylacetamido)ethylethoxy) siloxane]} and corresponding partial hydrolysates and also n-{α,ω-dihydroxyoligo[(1-(N-methylacetamido) ethylhydroxy)siloxane]}, n-{αω-dihydroxyoligo[(1-(²-pyrrolidonylethylhydroxy)siloxane]}, cyclo-{α, ω-dihydroxyoligo[(1-(2-pyrrolidonyl)ethylhydroxy) siloxane]}, cyclo- ({α, ω-dihydroxyoligo[(1-(N-methylacetamido)ethylhydroxy)siloxane])}, and mixtures thereof.

Preferred compounds of general formula III are: 1-(2-pyrrolidonyl)ethyl]-substituted and [1 -(N-methylacetamido)ethyl]-substituted D-, D/T- and T-oligo-andpolysilsesquioxanes and also poly[(1-(2-pyrrolidonyl) ethyl)siloxane] and poly[(l-(N-methylacetarnido)ethyl)-siloxane].

The present invention additionally provides for the use of the monomeric, oligomeric or polycondensed Si-containing compounds, or mixtures thereof, preferably in the form of aqueous or alcohol-containing solutions, as adhesion promoters between inorganic substances, for example glass, metals, metal oxides, solid metal hydroxides, ceramic, sandstone, concrete, bricks, clays, kaolin, cristobalite or wollastonite, and/or organic substances, for example epoxy resins, polyesters, polyurethanes, polyamides, cellulose, wood, paper, card, polyolefins, and also, outstandingly, for producing scratch-resistant and elastic coatings for the surface modification of the inorganic or organic substances.

Having generally described this invention, a further understanding can be obtained by reference to certain specific examples which are provided herein for purposes of illustration only and are not intended to be limiting unless otherwise specified.

EXAMPLES

Example 1

In a 2 l jacketed glass flask, with stirring, 605 mg (0.66 mmol, ratio 1:5700 relative to the starting materials) of tris(triphenylphosphine)rhodium(I) carbonyl hydride are added to 373 g (3.76 mol) of N-methyl-N-vinylacetamide and the mixture is heated to boiling (160° C. bottom temperature). 615 g (3.76 mol) of triethoxysilane are added dropwise over 4 hours, during which the reaction mixture heats up to 180° C., owing to the exothermic reaction, and pale yellow coloration appears. The progress of the reaction is monitored analytically by GC. The reaction mixture is subsequently left to react at the same temperature for one hour more, then cooled and trensferred to a shorts path distillation apparatus (Vigreux, without column section). Distillative purification gives 865 g (3.28 mol) of the target product N-1-(triethoxysilyl)ethyl-N-methylacetamide, corresponding to a yield of 87% by weight with respect to the starting materials.

Example 2

In a 1 l jacketed glass flask, with stirring, 200 mg (0.22 mmol, ratio 1:5700 relative to the starting materials) of tris(triphenylphosphine)rhodium(l) carbonyl hydride are added to 187 g (1.88 mol) of N-methyl-N-vinylacetamide and the mixture is heated to 110° C. (bottom temperature). 230 g (1.88 mol) of trimethoxysilane are added dropwise over 3.5 hours during which the reaction mixture heats up to 165° C., owing to the exothermic reaction, and a yellow coloration appears. The progress of the reaction is monitored analytically by GC. The reaction mixture is subsequently left to react at the same temperature for 2.5 hours more, then cooled and transferred to a short-path distillation apparatus (Vigreux, without column section). Distillative purification gives 325 g (1.47 mol) of the target product N-1-(trimethoxysilyl)ethyl-N-methylacetamide, corresponding to a yield of 78% by weight with respect to the starting materials.

Example 3

0.8 part by weight of N-1-(triethoxysilyl)ethyl-N-methylacetamide is introduced into 96 parts by weight of ethanol, and 3.2 parts by weight of distilled $H_2O$, adjusted beforehand with $CH_3COOH$ to a pH of 3.0 (measured using a pH stick) are added with stirring. Stirring is continued for 5 hours more until monomeric N-1-(triethoxysilyl)ethyl-N-methylacetamide can no longer be detected by GC. The solution obtained is then clear, colorless and ready to use.

The storage stability of the alcoholic oligosiloxane solution is >3 months.

Example 4

In a 500 ml jacketed glass flask, with stirring, 50 mg (0.1 l mmol, ratio 1:5000 relative to the starting materials) of $[Rh(1,5,-cyclooctadiene)Cl]_2$ are added to 55.6 g (0.5 mol) of N-vinyl-2-pyrrolidone and the mixture is heated to boiling (149° C. bottom temperature). 82.1 g (0.5 mol) of triethoxysilane are added dropwise over 0.5 hour, during which the reaction mixture heats up to 170° C., owing to the exothermic reaction, and pale yellow coloration appears. The progress of the reaction is monitored analytically by GC. The reaction mixture is subsequently left to react at the same temperature for 1.5 hours more, then cooled and transferred to a short-path distillation apparatus (Vigreux, without column section). Distillative purification gives 109 g (0.40 mol) of the target product N-1-(triethoxysilyl)ethyl-2-pyrrolidone, corresponding to a yield of 79% by weight with respect to the starting materials.

Example 5

A 500 ml laboratory steel autoclave is charged with 10 mg (0.02 mmol; ratio 1:25,000 relative to the starting materials) of $[Rh(1,5-cyclooctadiene)Cl]_2$ and 55.6 g (0.5 mol) of N-vinyl-2-pyrrolidone together with 82.1 g (0.5 mol) of triethoxysilane, and this initial charge is heated to 160° C. with stirring. It is left-to react for 1 hour during which the internal temperature of the reactor increases to 172° C. as a result of the exothermic reaction. The pressure measured during the reaction is from 1.0 to 2.0 bar. The reaction mixture is then left to cool over about 1 hour with stirring and is transferred to a short-path distillation apparatus (Vigreux, without column section). Distillative purification gives 106 g (0.38 mol) of the target product N-1-(triethoxysilylethyl-2-pyrrolidone, corresponding to a yield of 77% by weight with respect to the starting materials.

Example 6

A 500 ml laboratory steel autoclave is charged with 10 mg (0.02 mmol; ratio 1:25,000 relative to the vinyl-2-pyrrolidone employed) of $[Rh(1,5-cyclooctadiene)Cl]_2$ and 55.6 g (0.5 mol) of N-vinyl-2-pyrrolidone together with 90.4 g (0.55 mol) of triethoxysilane and 50 g (0.47 mol) of p-xylene, and this initial charge is heated to 160° C. with stirring. It is left to react for 3 hours, during which the internal temperature of the reactor increases to 180 ° C. as a result of the exothermic reaction. The pressure measured during the reaction is from 2.0 to 2.5 bar. The reaction mixture is then left to cool over about 1 hour with stirring and is transferred to a short-path distillation apparatus (Vigreux, without column section). Distillative purification gives 105 g (0.38 mol) of the target product N-1-(triethoxysilyl)ethyl-2-pyrrolidone, corresponding to a yield of 76% by weight with respect to the vinyl-2-pyrrolidone employed.

Example 7

In a 250 ml jacketed glass flask, with stirring, 3.3 mg (6.7 μmol, ratio 1:15,000 relative to the starting materials) of $[Rh(1,5-cyclooctadiene)Cl]_2$ are added to 16.4 g (0.1 mol) of triethoxysilane and the mixture is heated to a bottom temperature of 122° C. 11.1 g (0.1 mol) of N-vinyl-2-pyrrolidone are added dropwise over 2.5 hours, during which the reaction mixture heats up to 130° C., owing to the exothermic reaction, and pale yellow coloration appears. The progress of the reaction is monitored analytically by GC. The reaction mixture is subsequently left to react at the same temperature for 0.5 hour more, then cooled and transferred to a short-path distillation apparatus (Vigreux, without column section). Distillative purification gives 20.1 g (0.073 mol) of the target product N-1-(triethoxysilylethyl-2-pyrrolidone, corresponding to a yield of 73% by weight with respect to the starting materials.

Example 8

In a 4 l jacketed glass flask, with stirring, 420 mg (0.85 mmol, ratio 1:6300 relative to the starting materials) of $[Rh(1,5-cyclooctadiene)Cl]_2$ are added to 589 g (5.3 mol) of N-vinyl-2-pyrrolidone and the mixture is heated to boiling (149° C bottom temperature). 712 g (5.3 mol) of methyldiethoxysilane are added dropwise over 2.5 hours, during which the reaction mixture heats up to 190° C., owing to the exothermic reaction, and pale yellow coloration appears. The progress of the reaction is monitored analytically by GC. The reaction mixture is subsequently left to react at the same temperature for 2 hours more, then cooled and transferred to a short-path distillation apparatus (Vigreux, without column section). Distillative purification gives 1046 g (4.26 mol) of the target product N-1-(methyldiethoxysilyl)ethyl-2-pyrrolidone, corresponding to a yield of 80% by weight with respect to the starting materials.

Example 9

To prepare a 1% cyclocarboxamide-functional oligosiloxane solution, 5 g of N-1-(triethoxysilyl)ethyl-2-pyrrolidone are added dropwise to a mixture of 485 g of ethanol and 10 g of distilled water which has been adjusted before-hand with acetic acid to a pH of 2.5 (measured using pH sticks). The solution is stirred at room temperature for 2 hours and is then ready to use. The pH of the finished alcoholic oligosiloxane solution is about 6; the storage stability is >3 months.

Example 10

Plates of glass, copper and aluminum (measuring 7 ×15 cm), degreased beforehand with n-heptane, are dipped for 5 minutes each into the oligosiloxane solution obtained from Example 9. The plates are then placed up on edge and dried, followed by after treatment in the drying oven at 100° C. for one hour.

The result is a full-area coverage of the surface with a colorless, paint like siloxane film whose hardness was measured as being 5H (pencil test).

German Patent Applications 197 25 516.7, filed Jun. 17, 1997, and 197 42 974.2, filed Sep. 30, 1997, are both incorporated herein by reference in their entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be Secured by Letters Patent of the United States is:

1. An N-[ω-(methyl),ω-(silyl)]alkyl-N-organocarboxamide represented by formula I:

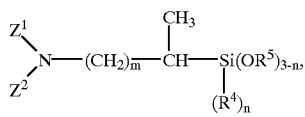

wherein $Z^1$ is

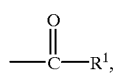

$Z^2$

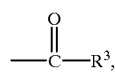

or $Z^1$ and $Z^1$ together with the nitrogen atom to which they are bonded form a ring represented by the formula:

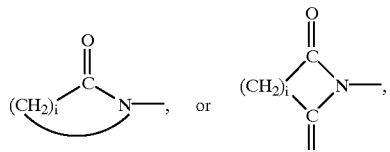

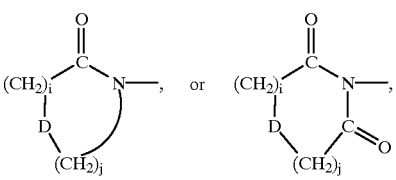

wherein D is a HN, O, S, SO or $SO_2$ group, i and j are each, independently, an integer from 0 to 7, and the size of the ring is ≦9 members, $R^1$, $R^2$, $R^3$, $R^4$ and $R^5$ are each, independently, a hydrogen atom, a linear, branched or cyclic alkyl group having 1 to 8 carbon atoms, or an aryl group having 6 to 10 carbon atoms, m is an integer from 0 to 16, and n is an integer from 0 to 3, with the proviso that (1) noncyclic compounds represented by formula I where m is 1 and (2) N-1-(triethoxysilyl)ethyl-2-pyrrolidone are excluded.

2. An oligomeric Si-containing compound represented by formula II:

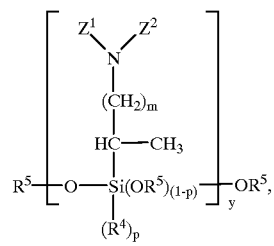

or a polycondensed Si-containing compound represented by formula III:

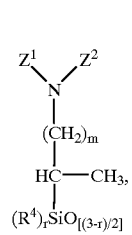

wherein
$Z^1$ is

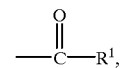

$Z^2$ is defined like $R^2$, or

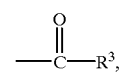

or $Z^1$ and $Z^2$ together with the nitrogen atom to which they are bonded form a ring represented by the formula:

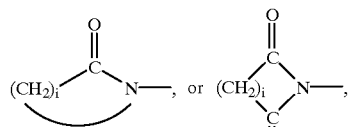

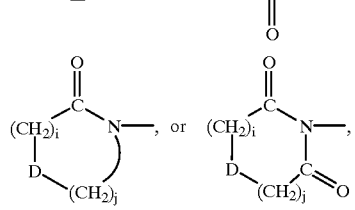

where D is a HN, O, S, SO or $SO_2$ group, i and j are each, independently, an integer from 0 to 7, and the size of the ring is ≦9 members, $R^1$, $R^2$, $R^3$, $R^4$ and $R^5$ are each, independently, a hydrogen atom, a linear, branched or cyclic alkyl group having 1 to 8 carbon atoms, or an aryl group having 6 to 10 carbon atoms, m is an integer from 0 to 16, p is 0 or 1, y is an integer from 2 to 50, and r is 0 or 1, with the proviso that compounds of formula III where m is 1, $Z^1$ is —$COR^1$ and $Z^2$ is — $COR^3$ are excluded.

3. A composition comprising an N-[ω-(methyl),ω-(silyl)]alkyl-N-organocarboxamide represented by formula I and at least one of (a) an oligomeric Si-containing compound represented by formula II and (b) a polycondensed Si-containing compound represented by formula III:

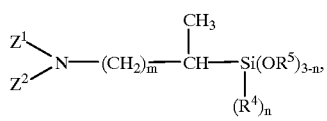
(I)

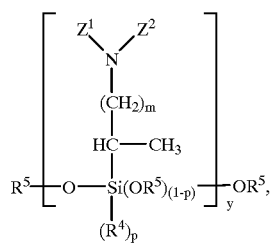
(II)

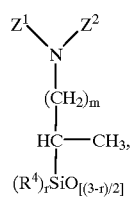
(III)

wherein $Z^1$ is

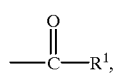

$Z^2$ is defined like $R^2$, or

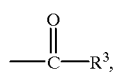

or $Z^1$ and $Z^2$ together with the nitrogen atom to which they are bonded form a ring represented by the formula:

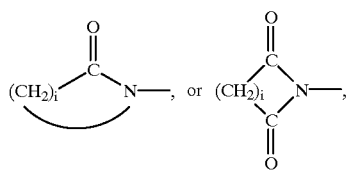

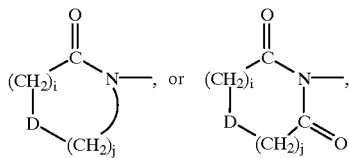

wherein D is a HN, O, S, SO or $SO_2$ group, i and j are each, independently, an integer from 0 to 7, and the size of the ring is $\leq 9$ members, $R^1$, $R^2$, $R^3$, $R^4$ and $R^5$ are each, independently, a hydrogen atom, a linear, branched or cyclic alkyl group having 1 to 8 carbon atoms, or an aryl group having 6 to 10 carbon atoms, m is an integer from 0 to 16, n is an integer from 0 to 3, p is 0 or 1, y is an integer from 2 to 50, and r is 0 or 1, with the proviso that
  (1) noncyclic compounds represented by formula I where m is 1 and (2) N-1-(triethoxysilyl)ethyl-2-pyrrolidone are excluded, and
  (2) compounds of formula III where m is 1, $Z^1$ is —COR' and $Z^2$ is —$COR^3$ are excluded.

4. A process for preparing a N-[ω-(methyl),ω-(silyl)]alkyl-N-organocarboxamide represented by formula I:

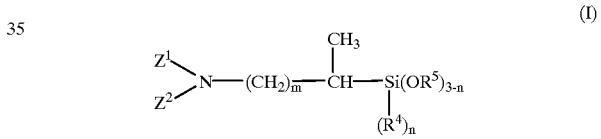
(I)

wherein $Z^1$ is

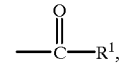

$Z^2$ is defined like $R^2$, or

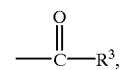

or $Z^1$ and $Z^2$ together with the nitrogen atom to which they are bonded form a ring represented by the formula:

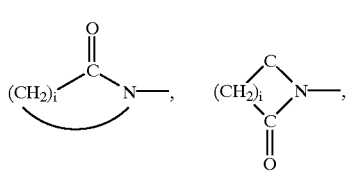

-continued

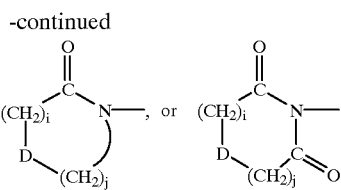

wherein D is a HN, O, S, SO or SO$_2$ group, i and j are each, independently, an integer from 0 to 7, and the size of the ring is ≦9 members, R$^1$, R$^2$, R$^3$, R$^4$ and R$^5$ are each, independently, a hydrogen atom, a linear, branched or cyclic alkyl group having 1 to 8 carbon atoms, or an aryl group having 6 to 10 carbon atoms, m is an integer from 0 to 16, and n is an integer from 0 to 3, with the proviso that (1) noncyclic compounds represented by formula I where m is 1 and (2) N-1-(triethoxysilyl)ethyl-2-pyrrolidone are excluded, comprising:

hydrosilylating an ω-alkylenecarboxamide represented by formula IV with a hydridosilane represented by formula V:

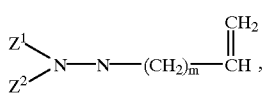 (IV)

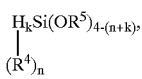 (V)

in the presence of a catalyst comprising rhodium, to produce the N-[ω-(methyl),ω-(silyl)]alkyl-N-organocarboxamide represented by formula I, wherein k is 1,2,3, or 4, and (n+k) ≦4.

5. The process of claim 4, wherein the catalyst comprises a rhodium complex.

6. The process of claim 4, wherein the catalyst comprises a member selected from the group consisting of metallic rhodium on an active carbon support, (Ph$_3$P)$_3$Rh(CO)H, (Ph$_3$P)$_3$RhCl, [Rh(1,5-cyclooctadiene)Cl]$_2$ and mixtures thereof.

7. The process of claim 6, wherein the catalyst further comprises at least one Pt complex.

8. The process of claim 7, wherein the catalyst contains a rhodium complex.

9. The process of claim 8, wherein the weight ratio of the Pt complex to the Rh complex is from 1:10 to 5:1.

10. The process of claim 7, wherein the Pt complex is selected from the group consisting of (Ph$_3$P)$_2$PtCl$_2$, (Ph$_3$P)$_4$Pt and Pt complexes based on hexachlorbplatinic acid.

11. The process of claim 7, wherein Pt complex is a compound based on hexachloroplatinic acid, as an acetone, cyclohexanone or isopropanol complex.

12. The process of claim 4, wherein the weight ratio of the catalyst to the ω-alkylenecarboxamide represented by formula IV is from 1:1000 to 1:100,000.

13. The process of claim 12, wherein the weight ratio of the catalyst to the ω-alkylenecarboxamide represented by formula IV is from 1:3000 to 1:50,000.

14. The process of claim 12, wherein the weight ratio of the catalyst to the ω-alkylenecarboxamide represented by formula IV is from 1:5000 to 1:30,000.

15. The process of claim 4, wherein the hydrosilylation is conducted in an inert hydrocarbon.

16. The process of claim 15, wherein the hydrosilylation is conducted in toluene, xylene or n-decane.

17. A process for preparing the oligomeric Si-containing compound represented by formula II or the polycondensed Si-containing compound represented by formula III as defined in claim 2, comprising:

subjecting at least one N-ω(methyl),ω-(silyl)]alkyl-N-organocarboxamide represented by formula I:

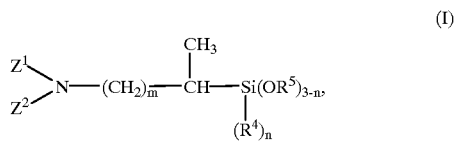 (I)

to hydrolysis in water or an alcohol/water mixture, wherein the weight ratio of the water to the alcohol is from 1:100 to 100:1 in the alcohol/water mixture, and the water or the alcohol/water mixture is adjusted to a pH <7 by addition of an inorganic or organic acid or an acidic salt or to a pH >7 by addition of a base or a basic salt, the weight ratio of the compound(s) of formula I to the water is from 0.1:99.9 to 99.99:0.01;

Z$^1$, Z$^2$, R$^4$, R$^5$, and m are as defined in claim 2, and n is an integer from 0 to 3.

18. The process of claim 17, wherein the pH is adjusted using hydrogen chloride, formic acid, acetic acid, citric acid, sodium hydroxide solution, sodium formate or sodium acetate.

19. The process of claim 17, wherein the pH of the water or alcohol/water mixture is adjusted to a value of ≧2 and ≦6.

20. The process of claim 17, wherein the compound(s) of formula I and water are employed in a proportion by mass to one another of from 10:90 to 99.9:0.1.

21. The process of claim 17, wherein an alcohol or an alcohol mixture is used where at least one of the alcohols corresponds to at least one alkoxy group of the compound of formula I employed.

22. The process of claim 17, wherein the alcohol is methanol, ethanol, propanol, butanol, 2-methoxyethanol, 2-ethylhexanol or a mixture thereof.

23. A process for preparing the composition of claim 3, comprising:

subjecting at least one N-ω(methyl),ω-(silyl)]alkyl-N-organocarboxamide represented by formula I:

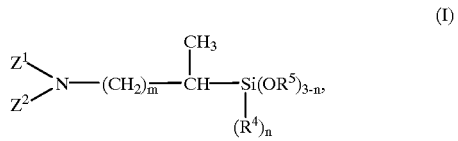 (I)

to controlled hydrolysis in water or an alcohol/water mixture, wherein the weight ratio of the water to the alcohol is from 1:100 to 100:1 in the alcohol/water mixture, and the water or the alcohol/water mixture is adjusted to a pH <7 by addition of an inorganic or organic acid or an acidic salt or to a pH >7 by addition of a base or a basic salt, the weight ratio of the compound(s) of formula I to the water is from 0.1:99.9 to 99.99:0.01, and $Z^1$, $Z^2$, $R^4$, $R^5$, m, and n are as defined in claim 3.

24. The process of claim 23, wherein the pH is adjusted using hydrogen chloride, formic acid, acetic acid, citric acid, sodium hydroxide solution, sodium formate or sodium acetate.

25. The process of claim 23, wherein the pH of the water or alcohol/water mixture is adjusted to a value of $\geq 2$ and $\leq 6$.

26. The process of claim 23, wherein the compound(s) of formula I and water are employed in a proportion by mass to one another of from 10:90 to 99.9:0.1.

27. The process of claim 23, wherein an alcohol or an alcohol mixture is used where at least one of the alcohols corresponds to at least one alkoxy group of the compound of formula I employed.

28. The process of claim 23, wherein the alcohol is methanol, ethanol, propanol, butanol, 2-methoxyethanol, 2-ethylhexanol or a mixture thereof.

29. A method of adhering substrates, comprising coating a first substrate with the oligomeric Si-containing compound represented by formula II or the polycondensed Si-containing compound represented by formula III as defined in claim 2 followed by contacting the coated first substrate with a second substrate, thereby causing adhesion of the first substrate to the second substrate.

30. A method of adhering substrates, comprising coating a first substrate with the composition of claim 3 followed by contacting the coated first substrate with a second substrate, thereby causing adhesion of the first substrate to the second substrate.

31. A method of forming a coating substrates, comprising coating a substrate with the oligomeric Si-containing compound represented by formula II or the polycondensed Si-containing compound represented by formula III as defined in claim 2.

32. A method of forming a coating substrates, comprising coating a substrate with the composition of claim 3.

33. An N-[ω-(methyl),ω-(silyl)]alkyl-N-organocarboxamide represented by formula I':

$$Z^1\diagdown_{N}\diagup Z^2 \quad CH_3 \atop | \atop —CH—Si(OR^5)_{3-n}, \atop | \atop (R^4)_n \qquad (I')$$

wherein $Z^1$ is $$—\overset{O}{\underset{\|}{C}}—R^1,$$

$Z^2$, $R^1$, $R^2$, $R^3$, $R^4$ and $R^5$ are each, independently, a hydrogen atom, a linear, branched or cyclic alkyl group having 1 to 8 carbon atoms, or an aryl group having 6 to 10 carbon atoms, and n is an integer from 0 to 3.

34. A method of adhering substrates, comprising coating a first substrate with a N-[ω-(methyl),ω-(silyl)]alkyl-N-organocarboxamide represented by formula I:

$$Z^1\diagdown_{N}\diagup Z^2 —(CH_2)_{\overline{m}}—\overset{CH_3}{\underset{|}{CH}}—Si(OR^5)_{3-n} \atop (R^4)_n \qquad (I)$$

wherein $Z^1$ is $$—\overset{O}{\underset{\|}{C}}—R^1,$$

$Z^2$ is defined like $R^2$, or $$—\overset{O}{\underset{\|}{C}}—R^3,$$

or $Z^1$ and $Z^2$ together with the nitrogen atom to which they are bonded form a ring represented by the formula:

$$(CH_2)_i\diagdown\overset{O}{\underset{\|}{C}}\diagup N—, \quad (CH_2)_i\diagdown\overset{\|}{\underset{\|}{C}}\diagup N—,$$

$$(CH_2)_i\diagdown\overset{O}{\underset{\|}{C}}\diagup N—, \text{ or } (CH_2)_i\diagdown\overset{O}{\underset{\|}{C}}\diagup N\diagdown_{C}\diagup(CH_2)_j\diagup O$$

wherein D is a HN, O, S, SO or $SO_2$ group, i and j are each, independently, an integer from 0 to 7, and the size of the ring is $\leq 9$ members, $R^1$, $R^2$, $R^3$, $R^4$ and $R^5$ are each, independently, a hydrogen atom, a linear, branched or cyclic alkyl group having 1 to 8 carbon atoms, or an aryl group having 6 to 10 carbon atoms, m is an integer from 0 to 16, and n is an integer from 0 to 3, with the proviso that (1) noncyclic compounds represented by formula I where m is 1 and (2) N-1-(triethoxysilyl)ethyl-2-pyrrolidone are excluded, followed by contacting the coated first substrate with a second substrate thereby causing adhesion of the first substrate to the second substrate.

35. A method of forming a coating on a substrate, comprising coating a substrate with a N-[ω-(methyl),ω-(silyl)]alkyl-N-organocarboxamide represented by formula I:

$$Z^1\diagdown_{N}\diagup Z^2 —(CH_2)_{\overline{m}}—\overset{CH_3}{\underset{|}{CH}}—Si(OR^5)_{3-n} \atop (R^4)_n \qquad (I)$$

wherein $Z^1$ is

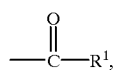

$Z^2$ is defined like $R^2$, or

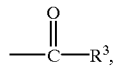

or $Z^1$ and $Z^2$ together with the nitrogen atom to which they are bonded form a ring represented by the formula:

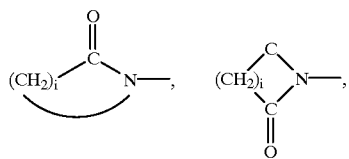

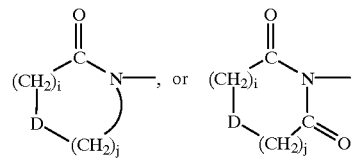

wherein D is a HN, O, S, SO or $SO_2$ group, i and j are each, independently, an integer from 0 to 7, and the size of the ring is $\leq 9$ members, $R^1$, $R^2$, $R^3$, $R^4$ and $R^5$ are each, independently, a hydrogen atom, a linear, branched or cyclic alkyl group having 1 to 8 carbon atoms, or an aryl group having 6 to 10 carbon atoms, m is an integer from 0 to 16, and n is an integer from 0 to 3, with the proviso that (1) noncyclic compounds represented by formula I where m is 1 and (2) N-1-(triethoxysilyl)ethyl-2-pyrrolidone are excluded.

* * * * *